United States Patent [19]
Takagi et al.

[11] Patent Number: 5,141,510
[45] Date of Patent: Aug. 25, 1992

[54] STRUCTURE OF ARTIFICIAL BONE MATERIAL FOR USE IN IMPLANTATION

[76] Inventors: Shigehide Takagi, 7-7, Tudanuma 3-Choume, Narashino-Shi, Chiba 275; Hideo Yano, 14-14, Nakaarai 5-Choume, Tokorozawa-Shi, Saitama 359; Kuniomi Ito, 3645-6, Tsuruta-Cho, Utunomiya-Shi, Tochigi 320; Kouichi Ohmamiuda, 15-5, Ouijidai 6-Choume, Sakura-shi Chiba 285; Tomohiko Iijima, 19-2, Moto-Nakayama, 3-Choume, Funabashi-shi, Chiba, 273, all of Japan

[21] Appl. No.: 460,054
[22] PCT Filed: May 29, 1989
[86] PCT No.: PCT/JP89/00533
 § 371 Date: Feb. 14, 1990
 § 102(e) Date: Feb. 14, 1990

[30] Foreign Application Priority Data
 May 27, 1988 [JP] Japan .................... 63-128230

[51] Int. Cl.⁵ .................... A61F 2/28; A61C 8/00
[52] U.S. Cl. .................... 623/16; 433/201.1
[58] Field of Search .................... 623/16,16D, 66; 433/201.1

[56] References Cited

U.S. PATENT DOCUMENTS

| 4,629,464 | 12/1986 | Takata et al. | 623/16 |
| 4,654,314 | 3/1987 | Takagi et al. | 623/16 X |
| 4,960,426 | 10/1990 | Atsumi | 623/16 |

FOREIGN PATENT DOCUMENTS 2158175  7/1987  Japan .................... 623/16 D

*Primary Examiner*—Roanald Frinks
*Attorney, Agent, or Firm*—Laurence R. Brown

[57] ABSTRACT

There is provided a structure of artificial bone for use in implanting or grafting bone comprising; a sintered body of calcium phosphate compounds; and hollowed minute tubes in said sintered body, having very small diameter, and extending along with a direction of Haversian canal extension of live organism, so as to produce two dimensional close-packed structure in said body, in form of cubic or hexagonal arrangement. The arrangement has in the sintered body of calcium phosphate compounds; hollowed minute tubes having a diameter of 0.1 to 2.0 mm, and the major portions thereof extending along with a direction of the Haversian canal extension, and producing a two dimensional close packed arrangement in said body against the face vertical to said direction, and being arranged with a separation, distance of 1.0 to 5.0 mm. The structure has preferably really spherical pores having diameter of 50 to 600 micrometer, and the porosity thereof being 0.5 to 40 percent.

3 Claims, 1 Drawing Sheet

STRUCTURE OF ARTIFICIAL BONE MATERIAL FOR USE IN IMPLANTATION

FIELD OF ART

The present invention relates to a structure of artificial bones for use in bone implantation or grafting, formed from calcium phosphate compounds. Particularly, it relates to an artificial bone structure for use in bone implantation or grafting, which can be applied at a bone position to which load or force is applied, and is useful in the medical fields especially in orthopaedics, plastics and oral surgery.

BACKGROUND OF THE ART

Compounds of calcium phosphate, including hydroxyapatite and tricalcium phosphate have the similar chemical properties to those of live bone and teeth in a living body or organism. The sintered body thereof has good bio-compatibility, and then, can be used as an alternative material used for artificial bone, bone aid and artificial roots, in form of a dense or porous body.

Such conventional calcium phosphate structure in dense body form can have enough strength necessary to support biologically dynamic movement, whereas there is not found new bone growth nor generation of bone tissue into the artificial dense bone structure. Further, generally, the adherent force to the living tissue where the artificial bones are inserted or implanted is dependent on the adhering force at the smooth interface thereof, and then it can not have the adherent function or force higher than that expected therefrom. On the other hand, a porous body of calcium phosphate compounds has somehow a limit of the dynamic strength, and then implantation of such porous body into a bone site of applied weight or load should be avoided, and sole use of the porous body should be avoided.

In order to enable sole use of an artificial bones at a bone site of applied mechanical load, it is necessary to provide a calcium phosphate compound to produce organization and structure having good bio-compatibility, and a method of compounding with organic or inorganic elastic material, and further to provide a material in use for compounding or integrating with the biological material. Such material, or porous ceramic material is disclosed in Japanese Patent Application No. 60-16879/1985.

DISCLOSURE OF INVENTION

The subject to be solved technologically by the present invention is the provision of the strong and tough structure of artificial bone produced from calcium phosphate compounds in which bone can be newly organized or grown into the bone structure, and then the artificial bone is well adhered to biological organism formation, and new bone organization can be well developed into the artificial bone.

Then, it is an object of the present invention to provide an artificial bone structure of calcium phosphate compounds which can evidence high mechanical strength when implanted in a bone tissue.

The inventive structure of artificial bone for use in implantation is provided for solving the above mentioned subject, and the present invention resides in a new structure of artificial bone for use in implantation or grafting of the bone, comprising a sintered body of calcium phosphate compounds; and hollowed minute tubes having diameters of 0.1 to 2.0 mm, and the major portions thereof extending along with a direction of Haversian canal extension, and producing two dimensional closely packed arrangements in said body against the surface vertical to said direction, and being arranged with separation, distances of 1.0 to 5.0 mm. Preferably, the internal structure of said sintered body has really spherical pores having diameters of 50 to 600 micrometers, and the porosity of said structure is preferably 0.5 to 40 percent.

Hereinafter, "calcium phosphate compounds" may include hydroxyapatite, tricalcium phosphate, tetracalcium phosphate, and further calcium phosphate compounds which can constitute the artificial bone.

SIMPLE DESCRIPTION OF DRAWINGS

FIG. 4A shows the close-packed arrangement of the tubes in cubic form while FIG. 4B shows the close packing in hexagonal arrangement.

BEST MODE FOR CARRYING OUT THE INVENTION

The starting material for producing the inventive structure having high strength, and high toughness may be porous bone ceramic material, for example, the ceramic material as disclosed in Japanese Patent Laid-open Publication No. 60-16879/1985. The present invention provides a specific structure to be applied to such material. The invention resides in the structure of the material for artificial bones, having a function to improve bio-compatibility and fusion ability to an organism or live tissue, which structure can be formed by providing small diameter tubular holes in one predetermined direction into a green body or sintered body in a process of manufacturing artificial bones from organic material, which holes can ensure growth of new bone tissue after implanted, and well flowing blood so as to grow uniformly new bone tissue.

The composition or structures of the tubular holes provided in provides one certain direction in the new structure of artificial bones are shown in FIGS. 1 to 4, can be explained as follows:

The small diameter tubular holes have preferably a diameter; d, as shown in FIG. 4, ranging 0.1 to 2.0 mm, and a suspension distance D, between the holes, as shown in FIG. 4, ranging 1.0 to 5.0 mm. More preferably, the diameter d is 1.0 to 3.0, and the distance D is 1.0 to 3.0 mm.

When the diameter d is lower than 0.1 mm, it will be possibly lower than the diameter of the bone tissue unit (osteon) including a Haversian canal, and then, is not preferable. When the diameter d is higher than 2.0 mm, the strength of the bone will be lowered, and then is not practical.

When the separation distance D is lower than 1.0 mm, the strength will be lowered similarly as above. When the distance D is higher than 3.0 mm, less number of Haversian canals can be formed to generate blood flow in the bone, and the distance is too great so that the uniform blood flow can not be generated.

Figures 3, 4A:
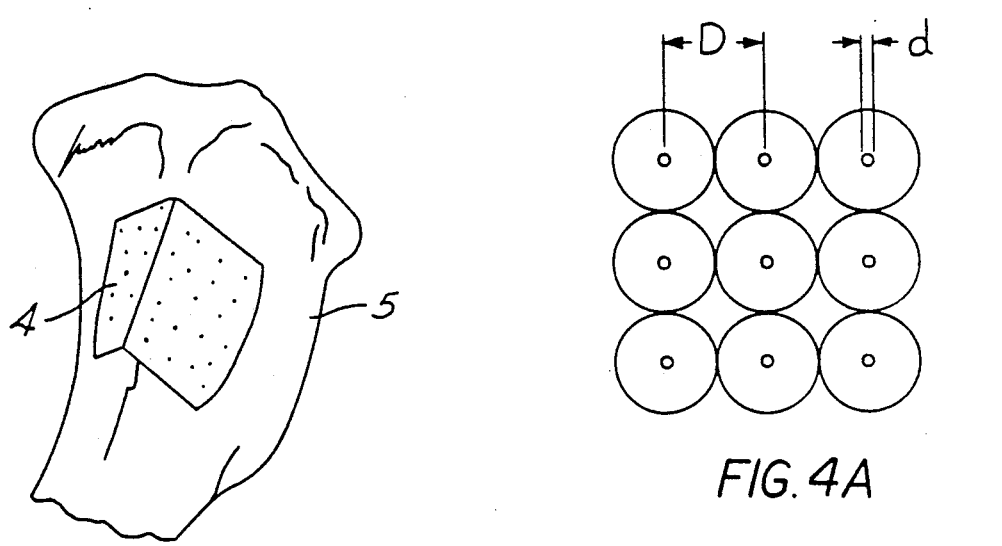
FIG. 3 illustrates schematically the living bone to which the inventive structure of calcium phosphate compounds was actually applied with high strength.
FIGS. 4A and 4B illustrate the close-packed arrangement of the hollowed tubes therein.
Figure 4B:
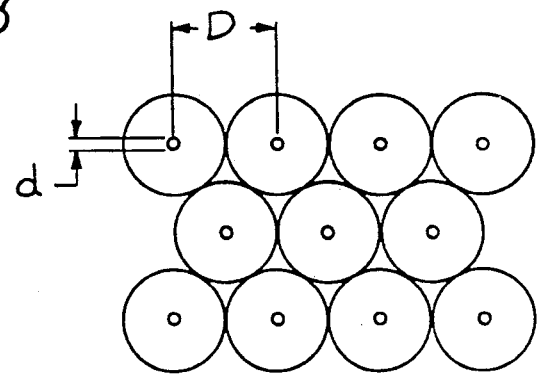

The tubular holes extend in a certain direction, which is corresponding to the direction along which Haversian canals extend. The arrangement of the tubular holes is that they are arranged in a close packing in a plane vertical to the direction in which the holes extends. The close-packed structure is as shown in FIGS. 4A and 4B, wherein FIG. 4A shows two dimensional cubic arrangement, and FIG. 4B shows two dimensional hexagonal arrangement. The distribution of the holes 2 is close-packed in a plane vertical to the direction along with which they extend. Such two-dimensional close packed structure is one of two alternatives, one is that the circles formed by the centers of the holes as a center of the circles are packed to form perfect squares, as shown in FIG. 4A, and the other is that the centers of the holes are packed to form perfect hexagons as shown in FIG. 4B.

The artificial bone implanted in a living body or organism, blood will flow in the tubular holes 2, in the structure as shown in FIGS. 4A and 4B, and then, bone formation is expected to grow around the holes 2, and therefore, there will be found new bone tissue growing easily in the structure of the implanted bone after implantation of the inventive artificial bone. In the other words, blood will flow uniformly in the structure of the implanted artificial bone, and will supply enough nutrient in the implanted artificial bone structure, so as to develop generation and growth of live bone tissue by activating osteoblast. Therefore, this can improve biocompatability and fusion with live tissue. Then, new bone formation will rapidly develop, and then, will improve complex strength of the artificial bone structure, and the adherent force with the bone surface can be ensured, and it will enable sole use at the site of applied dynamic load or force.

The material which can constitute the inventive bone structure can be produced, for example, as follows: a slurry of calcium hydroxide is mixed with phosphoric acid by titration, and by adjusting a reaction temperature, pH of the liquid so as to form hydroxyapatite, and the apatite is molded in a certain shape, which is fired into a sintered body.

As a starting material for the formation of the inventive bone structure, preferably the molar ratio of calcium to phosphorous is the range of 1.0 to 2.0 in the calcium phosphate compounds.

When the Ca/P molar ratio is less than 1.0, phosphoric acid will liberate to instabilize the compounds chemically. When the Ca/P molar ratio is higher than 2.0, calcium oxide will produced during firing as decomposition of the compound, and it will stimulate strongly the organism when implanted in the organism, thereby generating inflammation in the organism. Therefore, the range above 2.0 of Ca/P molar can not be used. Because of the above mentioned reasons, the preferable range for the Ca/P molar ratio is 1.0 to 2.0.

A concrete method of producing small diameter tubular holes in accordance with the present invention may comprise drilling holes extending in a certain direction, in a formed and sintered body of phosphate compound synthesized as mentioned above, by using a drill bar, and alternatively molding the material into a structure having small diameter tubular holes by using injection molding, or extrusion molding, or alternatively the process comprising molding the material into the structure containing resin fibers, and then burning the formed body so as to burn out the fibers in the body thereby producing small diameter tubular holes.

The method of producing a porous body of calcium phosphate compounds in accordance with the present invention will involve forming a sintered body containing spherical pores, and one of such formation process comprises forming a green body containing synthetic resin beads therein, and firing the green body so as to burn out the beads thereby producing spherical pores in the resulting fired body of calcium phosphate compounds. Further, synthetic fibers can be contained or mixed in the green body so as to form hollowed intercommunications, thereby enabling to produce the combination of spherical pores and intercommunications in the sintered structure. Therefore, as a synthetic resin, at least one of polypropylene, polymethylmethacrylate, polystyrene and polyethylene can be used.

The porosity depending on the spherical pores, in the sintered body is preferably 0.5 to 40 percent, and more preferably 5 to 35 percent. When the porosity is lower than 0.5 percent, the ratio of the interconnection of the pores is lowered. When the porosity is higher than 40 percent, the strength of the sintered body will be not enough to support the bone structure.

Figures 1A, 1B, 2:
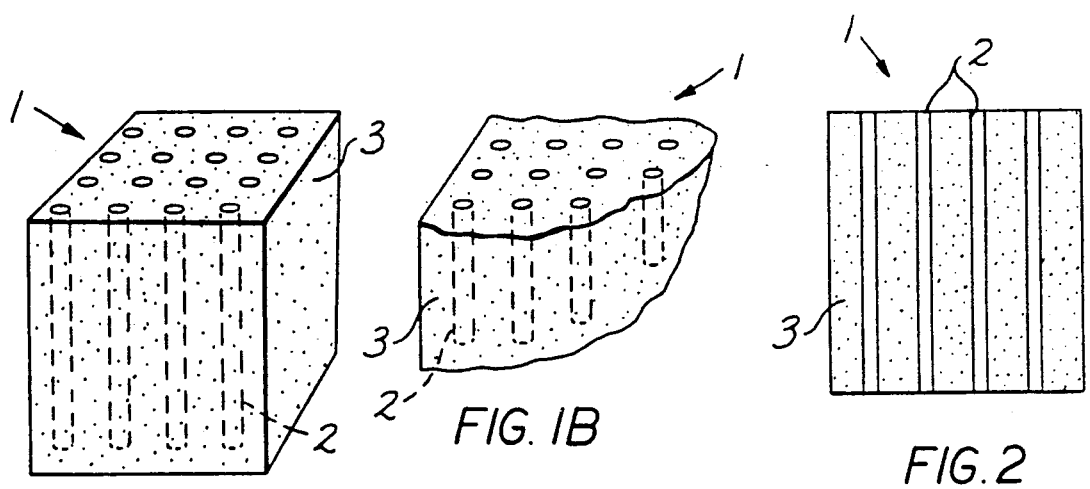
FIGS. 1A and 1B illustrate schematically the representative structure of the inventive artificial bone for use in implanting or grafting bone, which can have high strength and toughness.
FIG. 2 illustrates schematically the sectional view of the inventive structure of the artificial bone.

The inventive structure of artificial bones is illustrated in reference to the drawings. FIGS. 1A and 1B show a representative artificial bone for use in implantation, with high strength, as obtained in accordance with the present invention. A number of small diameter tubular holes 2 are provided in a certain direction in a sintered porous body of calcium phosphate, and further, among them a number of pores of sphere 3 and a number of hollowed intercommunications are provided in the body. FIG. 1A shows a cube 1 of the inventive artificial bone structure, from which desired shape of bones can be produced by machining. Alternatively, the desired shape of the bone can be produced by molding initially the material into the desired shape shown in FIG. 1B. The desired shape of the inventive bone can be used for implantation into a living bone or organ. FIG. 2 is a sectional view showing an internal structure of the inventive artificial bone structure. A number of small diameter holes or hollow tubes 2 extending in a certain direction are produced in the porous sintered body of calcium phosphate compounds by drilling the body of phosphate compounds or molding into a sintered body of phosphate compounds having a number of spherical pores 3 and hallowed intercommunications (not shown).

In FIGS. 1, 2, 3 and 4, 1 depicts a sintered body of calcium phosphate compounds, 2 depicts tubular holes or hollow tubes, 3 depicts pores of sphere, and 4 depicts the artificial bone used for implantation.

The structure of the artificial bone for use in implantation according to the present invention can be applied to insert, fill up, or cover a defect or removed portion of a living bone, and then new bone tissue can be expected to grow in a short time so as to produce enough strength of the artificial bone structure.

The bone structure of the present invention and the process for manufacturing the same are detailledly illustrated by the following example, which should not be interpreted for the limitation of the invention.

EXAMPLE

Powder of hydroxyapatite having a molar ratio of Ca to P of 1.67, as prepared by a wet process was mixed with spherical beads having diameter a of 50 to 250 micrometers, of methylmetharylate resin, and further pile (hair) of animal (cat) having diameter a of 5 micrometers and length of 50 micrometers, and the resulting mixture slurry was pressed at room temperature under Cold Isotropic Pressing of 300 kgf/cm$^2$ into a certain shape. The resulting shaped body was further cut into a cube of 20 mm, and the tubular holes were provided with a separation distance between the holes of about 3.0 mm, so as to form a green body. This green body is put in burning powder, and then sintered for about one hour at 1,150° C., and then, machined into a cube of 15 mm. This has a pressure strength of 800 kgf/cm$^2$.

The resulting artificial bone structure was used for implantation into a adult dog. A portion of (Corpus) tibia of the adult dog was removed at the edge of the inner portion in the length of 15 mm, in almost 3/5 of the sectional area, as shown in FIG. 3, and the inventive artificial bone cube produced as illustrated above was cut in an appropriate shape to the removed hollowed portion of the tibia, and the artificial bone was implanted into the tibia, as shown in FIG. 3. In the other words, the inventive bone structure 4 for use in implantation having small diameter tubular holes extending in one direction was implanted in the tibia bone 5 with matching the direction of the hole extension to the direction of Haversian canals extending in the live tibia bone 5.

At eight weeks after implantation, Xray observation revealed that a clear zone due to the removed bone disappeared. After 52 weeks passed, there was not found any defects such as crack, and damage in the bone.

The strength of the implanted bone was measured, and revealed that the pressure strength in one direction was 1,100 kgf/cm$^2$, and 1,150 kgf/cm$^2$ respectively when 12 weeks and 26 weeks passed after the operation. It revealed out that the inventive artificial bone structure has enough strength to support the dynamic load and durability.

The inventive structure of the artificial bone for implantation has been found to have the following function and effect.

Firstly, the holes extending along Haversian canals extending in the bone constitute bone acceptance holes in which blood can flow, thereby increasing the flow of blood in the bone and further developing the adherent force to the live tissue. Secondly, it can provide improved affinity and bio-compatibility with the live tissue, and can be applied solely to the situation at which weighting load is applied. Thirdly, new bone formation can grow rapidly in the implanted bone structure, and therefore, the strength of the bone complex structure can be rapidly increased, and at the same time the adherent force to the live bone will be developed and maintained. Therefore, it provides highly strong bone complex or structure.

Industrial Utilization

The inventive structure of artificial bone for use in implanting or grafting bone in a living body has the following industrial utilization.

Firstly, the holes extending along Haversian canals extending in the bone constitute bone acceptance holes in which blood can flow, thereby increasing the flow of blood in the bone and further developing the adherent force to the live tissue.

Secondly, it can provide improved affinity and bio-compatibility with the live tissue, and can be applied solely to the situation at which weighting load is applied.

Thirdly, new bone tissue can grow rapidly in the implanted bone structure, and therefore, the strength of the bone complex structure can be rapidly increased, and at the same time the adherent force to the live bone will be developed and maintained. Therefore, it provides highly strong bone complex or structure.

We claim:

1. A structure of artificial bone for use in implanting or grafting bone, comprising:
a sintered body of calcium phosphate compounds having spherical pores and hollowed intercommunications between pores having diameters of the order of a few micrometers, with hollowed minute tubes extending through said sintered body, having diameters of 0.1 to 2.0 mm, and extending along a direction of Haversian canals of a live organism for supporting the flow of blood for developing adherent force to the live organism, the tubes being spaced from one to five mm to produce close packing structure and high strength in said body.

2. The structure in accordance with claim 1, wherein said sintered body has spherical pores having diameter of 50 to 600 micrometer, and the porosity of said structure is 0.5 to 40 percent.

3. A structure of artificial bone, for use in implanting or grafting bone comprising:
a sintered body of calcium phosphate compounds having spherical pores and hollowed intercommunications between the pores having diameters of the order of a few micrometers, and
hollowed minute tubes formed in said sintered body, having diameter of 0.1 to 2.0 mm with axes thereof for extending along a direction of Haversian canals of a live organism to support a flow of blood encouraging development of an adherent force, and producing a two dimensional closely packed arrangement in said body in a plane normal to said direction having separation, distances of 1.0 to 5.0 mm.

* * * * *